United States Patent [19]

Cauwet et al.

[11] Patent Number: 5,368,850

[45] Date of Patent: Nov. 29, 1994

[54] AQUEOUS COSMETIC OR DERMATOLOGICAL DISPERSION FOR TREATMENT OF HAIR OR SKIN BASED ON SUGAR OR ALKYLSUGAR FATTY ACID ESTERS AND RETICULATED ACRYLAMIDE COPOLYMERS

[75] Inventors: Daniele Cauwet, Paris; Claude Dubief, Le Chesnay, both of France

[73] Assignee: L'Oreal, Paris, France

[21] Appl. No.: 151,847

[22] Filed: Nov. 15, 1993

[30] Foreign Application Priority Data

Nov. 13, 1992 [FR] France .................... 92 13706

[51] Int. Cl.$^5$ .................... A61K 7/06; A61K 7/42; A61K 7/075
[52] U.S. Cl. .................... 424/70; 424/59; 424/62; 424/71; 424/73; 424/78.31; 424/78.35; 514/859; 514/937
[58] Field of Search ............ 424/70, 71, 78.31, 78.35, 424/59, 62, 73; 514/859, 937

[56] References Cited

U.S. PATENT DOCUMENTS

| 4,450,090 | 5/1984 | Kinney . | |
| 5,089,252 | 2/1992 | Grollier et al. | 424/47 |
| 5,139,037 | 8/1992 | Grollier et al. | 132/203 |
| 5,160,730 | 11/1992 | Dubief et al. | 424/59 |

FOREIGN PATENT DOCUMENTS

| 0191564 | 8/1986 | European Pat. Off. . |
| 0424260 | 4/1991 | European Pat. Off. . |
| 4015733 | 11/1991 | Germany . |
| WO88/10147 | 12/1988 | WIPO . |

OTHER PUBLICATIONS

Cosmetic and Toiletries, vol. 100, Jun. 1985, pp. 55–59.
Seifen Öle Fette Wachse, vol. 117, No. 4, 1991, pp. 124–132.

*Primary Examiner*—John Kight, III
*Assistant Examiner*—Shelley A. Dodson
*Attorney, Agent, or Firm*—Jacobson, Price, Holman & Stern

[57] ABSTRACT

An aqueous cosmetic or dermatological dispersion for treatment of hair or skin contains the following in an aqueous medium:
a) at least one sugar or ($C_1$–$C_4$)alkylsugar, $C_4$–$C_{22}$ fatty acid mono and/or diester which may be oxyethylenated if necessary; and
b) at least one reticulated copolymer of acrylamide and a monomer selected from:
 (i) ammonium acrylate;
 (ii) partially or completely neutralized 2-acrylamido 2-methylpropane sulfonic acid;
 (iii) methacryloyl oxyethyl trimethylammonium chloride.

17 Claims, No Drawings

AQUEOUS COSMETIC OR DERMATOLOGICAL DISPERSION FOR TREATMENT OF HAIR OR SKIN BASED ON SUGAR OR ALKYLSUGAR FATTY ACID ESTERS AND RETICULATED ACRYLAMIDE COPOLYMERS

BACKGROUND OF THE INVENTION

1. Field of the Invention

The invention relates to an aqueous dispersion used as a cosmetic or in dermatology for treatment of hair or skin and based on sugar or alkylsugar fatty acid esters and reticulated acrylamide copolymers.

2. Description of the Prior Art

Sugar or alkylsugar fatty acid esters are known for their hair and skin conditioning properties. Their use in cosmetics is described in "Cosmetic and Toiletries, Vol. 100, June 1985, pages 55–59"; "Seifen Öle Fette Wachse, Vol. 117, No 4, 1991, pages 124–132", and in German patent application DE-A-4 015 733.

Polymers or cationic surfactants have long been used for softening hair or skin, facilitating combthrough of wet hair or styling of dry hair. Following repeated applications, however, cationic compounds dull the hair by rendering it sticky and also produce a sticky effect on skin.

It has surprisingly been discovered that a combination of sugar or alkylsugar fatty acid esters and certain reticulated acrylamide copolymers results in light and silky hair with considerably improved wet combthrough and dry styling properties.

Applying an aqueous dispersion of such a combination to the skin produces a soft feel with no stickiness.

Aqueous dispersions in accordance with the invention are easy to apply to the skin and hair. They are also remarkably stable; their cosmetic properties are retained over several successive applications.

One object of the invention is thus to provide an aqueous cosmetic or dermatological dispersion for treatment of hair or skin based on sugar and/or alkylsugar fatty acid mono and/or diesters and particular reticulated acrylamide copolymers.

A further object of the invention is to provide cosmetic hair or skin treatment methods using such compositions.

Further objects of the invention will become apparent from the description given and examples given later.

SUMMARY OF THE INVENTION

The invention consists in an aqueous cosmetic or dermatological dispersion for treatment of hair or skin containing in a cosmetically or physiologically acceptable medium:

a) at least one sugar or ($C_1$–$C_4$)alkylsugar, $C_4$–$C_{22}$ fatty acid mono and/or diester which may be oxyethylenated if necessary; and b) at least one reticulated copolymer of acrylamide and a monomer selected from:
 (i) ammonium acrylate;
 (ii) partially or completely neutralized 2-acrylamido 2-methylpropane sulfonic acid;
 (iii) methacryloyl oxyethyl trimethylammonium chloride.

The following sugar or ($C_1$–$C_4$)alkylsugar, $C_4$–$C_{22}$ fatty acid esters may be used in the present invention:

(1) ($C_1$–$C_4$)alkylglucosyl esters such as:
-methylglucosyl monostearate, as sold for example by GRILLO-WERKE under the trade name GRILLOCOSE IS;
-methylglucosyl sesquistearate, as sold for example by AMERCHOL under the trade name GLUCATE SS;
-6-ethylglucosyl decanoate, as sold for example by NOVO under the trade name BIOSURF 10;
-6-ethylglucosyl stearate, as sold for example by NOVO under the trade name BIOSURF 18;
-a mixture of 6-ethylglucosyl mono- and dicocoate (82/7), as sold for example by NOVO under the trade name BIOSURF COCO;
-a mixture of 6-ethylglucosyl mono- and dilaurate, as sold for example by NOVO under the trade name BIOSURF 12;
-$C_{12}$–$C_{18}$ fatty acid monoesters of butylglucoside, such as butylglucosyl monococoate, as sold for example by REWO under the trade name REWOPOL V3101 or REWOSAN V3101, and butylglucosyl monococoate polyoxyethylenated with 3 moles of ethylene oxide, such as sold for example by REWO under the trade name REWOPOL V3122.

(2) Glucose esters such as:
O-hexadecanoyl-6-D-glucose,
O-octanoyl-6-D-glucose,
O-oleyl-6-D-glucose,
O-linoleyl-6-D-glucose,
which are known compounds and which may for example be prepared from the corresponding acid and D-glucose following the method described by E REINEFELD et al in "Die Stärke", No 6, pages 181–189, 1968.

(3) Monoesters of saccharose, such as:
Saccharyl monolaurate as sold for example by GRILLO-WERKE under the trade name GRILLOTEN LSE 65 and saccharyl monococoate as sold for example by GRILLO-WERKE under the trade name GRILLOTEN LSE 65K.

Particularly preferred sugar or ($C_1$–$C_4$)alkylsugar fatty acid esters are selected from $C_{12}$–$C_{18}$ fatty acid monoesters of butylglucoside and methylglucosyl monostearate.

(4) Sucroglycerides, such as:
Product mixtures obtained directly from transesterification between saccharose and natural or synthetic triglycerides. These mixtures are primarily constituted by monoesters and diesters of saccharose and small quantities of unaltered monoglycerides, diglycerides and triglycerides. The term triglyceride means one or more triglycerides of saturated or unsaturated aliphatic fatty acids having at least, 12 carbon atoms, preferably 14 to 22 carbon atoms. These compounds may be prepared as described in French patent FR-A-2 463 152.

Examples of natural triglycerides are palm oil, castor oil, coconut oil or colza oil. Particularly preferred products are those resulting from transesterification of palm oil by saccharose sold under the trade name MIRASOFT by RHONE POULENC.

Sugar or ($C_1$–$C_4$)alkylsugar fatty acid esters in accordance with the invention are present in the aqueous dispersions in concentrations of between 0.1 and 20%, preferably between 0.5 and 10% by weight with respect to the total composition weight.

The reticulated acrylamide/ammonium acrylate copolymer used in accordance with the invention is more particularly an acrylamide/ammonium acrylate copolymer (5/95 by weight) reticulated using a polyunsaturated olefinic reticulating agent such as divinylbenzene, tetraallyloxyethane, methylene bis-acrylamide, diallyl ether, polyallylpolyglyceryl ethers or allyl ethers of alcohols of the sugar series such as erythritol, pentaerythritol, arabitol, mannitol, sorbitol glucose.

Analogous copolymers and their preparation are described in French patent FR-A-2 416 723 and U.S. Pat. Nos. 2,798,053 and 2,923,692.

This reticulated copolymer is in preferably used in the form of a water-in-oil emulsion constituted by 30% by weight of said copolymer, 25% by weight of paraffin, 4% by weight of a mixture of sorbityl stearate and a hydrophilic ethoxylated derivative, and 41% by weight of water. Such an emulsion is marketed under the trade name PAS 5161 or BOZEPOL C by HOECHST.

Copolymers of acrylamide and 2-acrylamido 2-methylpropane sulfonic acid used in accordance with the present invention are copolymers which have been reticulated using a polyunsaturated olefinic compound such as those described above, and partially or totally neutralized by a neutralizing agent such as caustic soda, potash, ammonia or an amine such as triethanolamine or monoethanolamine.

They can be prepared by copolymerizing acrylamide and sodium 2-acrylamido 2-methylpropanesulfonate by a radical pathway using azobis-isobutyronitrile type initiators and precipitation from an alcohol such as tertiobutanol.

Copolymers obtained from copolymerization of 70 to 55 mole % of acrylamide and 30 to 45 mole % of sodium 2-acrylamido 2-methylpropanesulfonate are particularly preferred; the reticulating agent is used in concentrations of $10^{-4}$ to $4.10^{-4}$ mole per mole of monomer mixture.

These preferred copolymers are preferably incorporated in the aqueous dispersion of the invention in the from of oil-in-water emulsions containing 35 to 40% by weight of copolymer, 15 to 25% by weight of a mixture of $C_{12}-C_{13}$ isoparaffinic hydrocarbons, 3 to 8% by weight of polyethyleneglycol laurylether with 7 moles of ethylene oxide and water, such as the emulsion marketed under the trade name SEPIGEL 305 by SEPPIC.

The reticulated acrylamide and methacryloyl oxyethyl trimethylammonium chloride copolymer used in the present invention is more particularly a copolymer obtained by copolymerization of acrylamide and dimethylaminoethylmethacrylate quaternized with methyl chloride, followed by reticulation with an unsaturated olefinic compound, particularly methylene-bis acrylamide.

A reticulated acrylamide/methacryloyl oxyethyl trimethylammonium chloride copolymer (20/80 by weight) may be used in the form of a dispersion containing 50% by weight of said copolymer in mineral oil marketed under the trade name SALCARE SC92 by ALLIED COLLOIDS.

Reticulated acrylamide copolymers as described above are present in aqueous dispersions of the invention in concentrations of active material of between 0.05 and 10%, preferably between 0.1 and 5% by weight with respect to the total dispersion weight.

The dispersions of the invention may also contain additives in normal use in cosmetics or in dermatology such as perfumes, dyes, preservatives, sequestrating agents, animal, vegetable or synthetic oils, perfluoropolyethers, ceramides, solar filters, free radical absorbers, anionic, nonionic, amphoteric or cationic surfactants, polymers, proteins, packaging agents, foam stabilizers and propellants.

Cosmetic or dermatological dispersions for use on the hair may be used in the form of wash products such as shampoos, or rinses to apply before or after shampooing and before, during or after dyeing or bleaching, before or after perming or straightening or as an intra perm lotion.

Cosmetic or dermatological dispersions for use on the hair may also be used in the form of non-wash products such as setting or blow drying lotions.

These dispersions are preferably applied using a method including a rinse.

Cosmetic or dermatological dispersions in accordance with the invention for use in treating and caring for the skin may be packaged as a bath or shower product, a shaving product, a perfumed lotion, or a skin care cream or milk.

Dispersions in accordance with the invention may be applied topically. They contain an effective quantity of a dermatologically active substance such as vitamin A, carotenoids, natural pigments, retinoids, depigmentizers, antiseborrheic agents, antiacne agents, antiinflammatory agents or antipellicular agents.

Cosmetic or topical dispersions according to the invention have a pH of between 3 and 10, preferably 5 to 7. This pH may be adjusted by alkalizing or acidulating agents normally used in cosmetics or in dermatology.

A cosmetic treatment for hair in accordance with the invention consists in applying compositions as defined above to the hair, depending on the desired purpose (shampoo, hair lotion, etc), and then rinsing the hair if necessary.

A cosmetic skin treatment according to the invention consists in applying to it a composition as described above, depending on the desired purpose, and rinsing if necessary.

DETAILED DESCRIPTION OF THE INVENTION

The following examples are intended to illustrate the invention but not to limit its scope.

EXAMPLE 1

HAIR CARE LOTION

| | |
|---|---|
| Butylglucosyl monococoate, sold as 100% AM under the trade name REWOSAN V3101 by REWO | 10 g |
| Oil-in-water emulsion of reticulated acrylamide/sodium 2-acrylamido 2-methyl-propane sulfonate copolymer, sold as about 40% copolymer under the trade name SEPIGEL 305 by SEPPIC | 0.5 g of copolymer |
| Perfume, preservative | qs |
| Water | qsp 100 g |
| Spot pH = 6.5 | |

EXAMPLE 2

HAIR CARE LOTION

| | |
|---|---|
| Methylglucosyl monostearate, sold as 100% AM under the trade name GRILLOCOSE IS by GRILLOWERKE | 5 g |
| Water-in-oil emulsion of reticulated acrylamide/ammonium acrylate copolymer, sold as 30% copolymer under the trade name PAS 5161 by HOECHST | 0.3 g of copolymer |

-continued

| | | |
|---|---|---|
| Perfume, preservative | qs | |
| Water | qsp | 100 g |
| Spot pH = 6.8 | | |

EXAMPLE 3
HAIR CARE GEL

| | | |
|---|---|---|
| Methylglucosyl monostearate, sold as 100% AM under the trade name GRILLOCOSE IS by GRILLOWERKE | 0.5 g | |
| Dispersion of reticulated acrylamide/ methacryloyloxyethyl trimethylammonium chloride copolymer in mineral oil, sold as 50% copolymer under the trade name SALCARE SC92 by ALLIED COLLOIDS | 1 g of copolymer | |
| Perfume, preservative | qs | |
| Water | qsp | 100 g |
| Spot pH = 4 | | |

EXAMPLE 4
HAIR CARE LOTION

| | | |
|---|---|---|
| Butylglucosyl monococoate, sold as 100% AM under the trade name REWOPOL V3101 by REWO | 1 g | |
| Oil-in-water emulsion of reticulated acrylamide/sodium 2-acrylamido 2-methyl-propane sulfonate copolymer, sold as about 40% copolymer under the trade name SEPIGEL 305 by SEPPIC | 1 g of copolymer | |
| Perfume, preservative | qs | |
| Water | qsp | 100 g |
| NaOH | qs | pH = 7 |

EXAMPLE 5
HAIR CARE GEL

| | | |
|---|---|---|
| Methylglucosyl monostearate, sold as 100% AM under the trade name GRILLOCOSE IS by GRILLO-WERKE | 1 g | |
| Oil-in-water emulsion of reticulated acrylamide/sodium 2-acrylamido 2-methyl-propane sulfonate copolymer, sold as about 40% copolymer under the trade name SEPIGEL 305 by SEPPIC | 1 g of copolymer | |
| Perfume, preservative | qs | |
| Water | qsp | 100 g |
| HCl | qs | pH = 7.5 |

EXAMPLE 6
HAIR CARE GEL

| | | |
|---|---|---|
| Methylglucosyl sesquistearate, sold as 100% AM under the trade name GLUCATE SS by AMERCHOL | 1 g | |
| Oil-in-water emulsion of reticulated acrylamide/sodium 2-acrylamido 2-methyl-propane sulfonate copolymer, sold as about 40% copolymer under the trade name SEPIGEL 305 by SEPPIC | 1 g | |
| Perfume, preservative | qs | |
| Water | qsp | 100 g |
| HCl | qs | pH = 5 |

EXAMPLE 7
HAIR CARE GEL

| | | |
|---|---|---|
| Ethylglucosyl mono/dilaurate (84/8), sold as 100% AM under the trade name BIOSURF 12 by NOVO | 1 g | |
| Oil-in-water emulsion of reticulated acrylamide/sodium 2-acrylamido 2-methyl-propane sulfonate copolymer, sold as about 40% copolymer under the trade name SEPIGEL 305 by SEPPIC | 1 g | |
| Perfume, preservative | qs | |
| Water | qsp | 100 g |
| HCl | qs | pH = 5 |

EXAMPLE 8
HAIR CARE GEL

| | | |
|---|---|---|
| Ethylglucosyl mono/dicocoate (82/7), sold as 100% AM under the trade name BIOSURF COCO by NOVO | 1 g | |
| Oil-in-water emulsion of reticulated acrylamide/sodium 2-acrylamido 2-methyl-propane sulfonate copolymer, sold as about 40% copolymer under the trade name SEPIGEL 305 by SEPPIC | 1 g | |
| Perfume, preservative | qs | |
| Water | qsp | 100 g |
| HCl | qs | pH = 5 |

EXAMPLE 9

| | | |
|---|---|---|
| Monococoate of saccharose, sold as GRILLOTEN LSE 65K by GRILLO-WERKE | 10 g AM | |
| Oil-in-water emulsion of reticulated acrylamide/sodium 2-acrylamido 2-methyl-propane sulfonate copolymer, sold as about 40% copolymer under the trade name SEPIGEL 305 by SEPPIC | 1 g AM | |
| Water | qsp | 100 g |
| HCl | | pH = 5 |

EXAMPLE 10

| | | |
|---|---|---|
| O-oleyl-6-D-glucose | 5 g AM | |
| Dispersion of reticulated acrylamide/ methacryloyloxyethyl trimethylammonium chloride copolymer in mineral oil, sold as 50% copolymer under the trade name SALCARE SC92 by ALLIED COLLOIDS | 2 g AM | |
| Water | qsp | 100 g |
| NaOH | | pH = 6 |

EXAMPLE 11

| | | |
|---|---|---|
| Triglyceride esters of palm and saccharose, sold under the trade name MIRASOFT MSP 11 by RHONE POULENC | 5 g AM | |
| Water-in-oil emulsion of reticulated acrylamide/ammonium acrylate copolymer, sold as 30% copolymer under the trade name PAS 5161 by HOECHST | 1 g AM | |
| Water | qsp | 100 g |
| NaOH | | pH = 7 |

There is claimed:

1. An aqueous dispersion for the cosmetic treatment of hair or the skin and/or in dermatology, which contains in a cosmetically or physiologically acceptable medium:
   a) at least one sugar or ($C_1$-$C_4$)alkylsugar, $C_4$-$C_{22}$ fatty acid mono and/or diester which may be oxyethylenated if necessary; and
   b) at least one reticulated copolymer of acylamide and a monomer selected from:
      (i) ammonium acrylate;
      (ii) partially or completely neutralized 2-acrylamido 2-methylpropane sulfonic acid;
      (iii) methacryloyl oxyethyl trimethylammonium chloride.

2. Dispersion according to claim 1 wherein said sugar or alkylsugar fatty acid esters are selected from mono- and diesters of ($C_1$-$C_4$)alkylglucoside, monoesters and diesters of saccharose and esters of glucose.

3. Dispersion according to claim 1 wherein said sugar or alkylsugar fatty acid esters are selected from $C_{12}$-$C_{18}$ fatty acid monoesters of butylglucoside and methylglucosyl monostearate.

4. Dispersion according to claim 1 wherein said fatty acid esters are selected from mixtures of mono- and diesters of $C_{14}$-$C_{22}$ fatty acids of saccharose and the composition further contains mono-, di- and triglycerides of $C_{14}$-$C_{22}$ fatty acids.

5. Dispersion according to claim 1 wherein said sugar or alkylsugar fatty acid mono and/or diester, which may be oxyethylenated if required, is present in concentrations of between 0.1 and 20% by weight with respect to the total dispersion weight.

6. Dispersion according to claim 1 wherein said acrylamide copolymer is reticulated using a polyunsaturated olefinic reticulating agent selected from divinylbenzene, tetraallyloxyethane, methylene bis-acrylamide, diallyl ether, polyallylpolyglyceryl ethers or allyl ethers of alcohols of the sugar series.

7. Dispersion according to claim 1 containing a reticulated acrylamide/ammonium acrylate copolymer (5/95 by weight) in the form of a water-in-oil emulsion comprising 30% by weight of said copolymer, 25% by weight of paraffin oil, 4% by weight of a mixture of sorbityl stearate and a hydrophilic ethoxylated derivative and 41% by weight of water.

8. Dispersion according to claim 1 containing a reticulated acrylamide/2-acrylamido 2-methylpropane sulfonic acid copolymer which is partially or completely neutralized by caustic soda, potash, ammonia or an amine and is in the form of an oil-in-water emulsion containing 35 to 45% by weight of said copolymer, 15 to 25% by weight of a mixture of $C_{12}$-$C_{13}$ isoparaffinic hydrocarbons, 3 to 8% by weight of polyethyleneglycol laurylether with 7 moles of ethylene oxide, and water.

9. Dispersion according to claim 1 containing a reticulated acrylamide/methacryloyl oxyethyl trimethylammonium copolymer (20/80 by weight) in the form of a dispersion containing 50% of said copolymer in mineral oil.

10. Dispersion according to claim 1 containing 0.05 to 10% by weight of reticulated acrylamide copolymer as active material.

11. Dispersion according to claim 1 further containing an additive in normal use in cosmetics or in dermatology selected from perfumes, dyes, preservatives, sequestrating agents, animal, vegetable or synthetic oils, perfluoropolyethers, ceramides, solar filters, free radical absorbers, anionic, nonionic, amphoteric or cationic surfactants, polymers, proteins, packaging agents, foam stabilizers and propellants.

12. Dispersion according to claim 1 having a pH of between 3 and 10.

13. Dispersion according to claim 1 for the treatment of hair packaged as a shampoo, as a rinse product for application before or after shampooing, before, during or after dyeing or bleaching, before or after perming or straightening, as an intra perm lotion, as a setting lotion or as a blow drying lotion.

14. Dispersion according to claim 1 for the treatment of skin packaged as a bath or shower product, as a shaving product, as a skin care cream or milk or as a perfumed lotion.

15. Cosmetic hair treatment method in which a dispersion is applied to the hair which is then rinsed if necessary, said dispersion containing in a cosmetically or physiologically acceptable medium:
   a) at least one sugar or ($C_1$-$C_4$)alkylsugar, $C_4$-$C_{22}$ fatty acid mono and/or diester which may be oxyethylenated if necessary; and
   b) at least one reticulated copolymer of acrylamide and a monomer selected from:
      (i) ammonium acrylate;
      (ii) partially or completely neutralized 2-acrylamido 2-methylpropane sulfonic acid;
      (iii) methacryloyl oxyethyl trimethylammonium chloride, and being packaged as a shampoo, as a rinse product for application before or after shampooing, before, during or after dyeing or bleaching, before or after perming or straightening, as an intra perm lotion, as a setting lotion or as a blow drying lotion.

16. Cosmetic skin treatment method in which a dispersion is applied to the skin, said dispersion containing in a cosmetically or physiologically acceptable medium:
   a) at least one sugar or ($C_1$-$C_4$)alkylsugar, $C_4$-$C_{22}$ fatty acid mono and/or diester which may be oxyethylenated if necessary; and
   b) at least one reticulated copolymer of acrylamide and a monomer selected from:
      (i) ammonium acrylate;
      (ii) partially or completely neutralized 2-acrylamido 2-methylpropane sulfonic acid;
      (iii) methacryloyl oxyethyl trimethylammonium chloride, and being packaged as a bath or shower product, as a shaving product, as a skin care cream or milk or as a perfumed lotion.

17. Dispersion according to claim 1 for use as a dermatological composition in the form of an aqueous dispersion and further containing a dermatologically active substance.

* * * * *